US009457054B2

(12) United States Patent
Schmidt et al.

(10) Patent No.: US 9,457,054 B2
(45) Date of Patent: Oct. 4, 2016

(54) **METHOD FOR USING A *BACILLUS SUBTILIS* STRAIN FOR PROPHYLAXIS AND TREATMENT OF GASTRO-INTESTINAL CONDITIONS**

(75) Inventors: Joseph Earl Schmidt, Davis, CA (US); Desmond Rito Jimenez, Woodland, CA (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 13/582,359

(22) PCT Filed: Mar. 17, 2011

(86) PCT No.: PCT/US2011/028755
§ 371 (c)(1),
(2), (4) Date: Aug. 31, 2012

(87) PCT Pub. No.: WO2011/116155
PCT Pub. Date: Sep. 22, 2011

(65) Prior Publication Data
US 2012/0328571 A1 Dec. 27, 2012

Related U.S. Application Data

(60) Provisional application No. 61/314,997, filed on Mar. 17, 2010.

(51) Int. Cl.
*A61P 1/06* (2006.01)
*A61K 35/74* (2015.01)

(52) U.S. Cl.
CPC ..................... *A61K 35/74* (2013.01)

(58) Field of Classification Search
CPC ...................................... A61K 35/74
USPC .................. 424/93.2, 93.3, 93.462
See application file for complete search history.

(56) References Cited

U.S. PATENT DOCUMENTS

| | | | |
|---|---|---|---|
| 4,919,936 A | 4/1990 | Iwanami et al. | |
| 6,015,553 A | 1/2000 | Germida et al. | |
| 6,060,051 A | 5/2000 | Heins et al. | |
| 6,103,228 A | 8/2000 | Heins et al. | |
| 6,156,333 A | 12/2000 | Langrehr | |
| 6,291,426 B1 | 9/2001 | Heins et al. | |
| 6,417,163 B1 | 7/2002 | Heins et al. | |
| 6,422,174 B1 | 7/2002 | Horikawa et al. | |
| 6,461,607 B1 | 10/2002 | Farmer | |
| 6,638,910 B2 | 10/2003 | Heins et al. | |
| 6,660,294 B2 | 12/2003 | Maruta et al. | |
| 7,247,299 B2 | 7/2007 | Lin et al. | |
| 2003/0147923 A1 | 8/2003 | Klaviniskis et al. | |
| 2003/0194424 A1 | 10/2003 | Lis et al. | |
| 2004/0101525 A1* | 5/2004 | Lin et al. | 424/115 |
| 2004/0247582 A1 | 12/2004 | Binder et al. | |
| 2005/0031601 A1 | 2/2005 | Wynne et al. | |
| 2005/0031732 A1 | 2/2005 | Suhr-Jessen et al. | |
| 2007/0065540 A1 | 3/2007 | Jones et al. | |
| 2007/0298013 A1* | 12/2007 | Altman | 424/93.3 |
| 2008/0057047 A1 | 3/2008 | Sas et al. | |
| 2010/0092428 A1 | 4/2010 | Schmidt et al. | |
| 2010/0143417 A1 | 6/2010 | James et al. | |
| 2012/0321592 A1 | 12/2012 | Schmidt et al. | |

FOREIGN PATENT DOCUMENTS

| | | |
|---|---|---|
| EP | 0287699 A2 | 10/1998 |
| JP | S62-232343 A | 12/1987 |
| JP | H04166080 | 6/1992 |
| JP | 2000166583 A | 6/2000 |
| JP | 2007-054041 | 5/2007 |
| JP | 2007236286 A | 9/2007 |
| RU | 2266747 C1 | 12/2005 |
| WO | WO9850422 A1 * | 11/1998 |
| WO | 00/29426 A1 | 5/2000 |
| WO | 2009037242 A2 | 3/2009 |
| WO | 2010/068231 A1 | 6/2010 |
| WO | 2011/116155 WO | 9/2011 |

OTHER PUBLICATIONS

Biopesticide Registration Action Document Bacillus subtilis Strain QST 713 (PC Code 006479) www.epa.gov/pesticides/chem . . . /decision_PC-006479_9-Aug. 6.pdf.*
U.S. Appl. No. 12/508,080, Lin et al.
Kim, S., et al., "Selection and Characterization of Bacillus Probiotics for Human and Animal Feed,"Abstract of the General Meeting of the American Society for Microbiology, (2001) p. 550, vol. 101.
Bacillus subtilis strain QST 713 European Monograph, Bundesamt für Verbraucherschutz and Lebensmittelsicherheit (BVL), 2001 [retrieved on Jun. 13, 2012]. Retrieved from the Internet:< URL: http://www.bvl.bund.de/SharedDocs/Downloads/04__Pflanzenschutzunittel/02__eu_berichte/Bacsub-Dar.pdf?__blob=publicationFile&v=2> Annex B, pp. 127-134
New microbial offers alternative to AGPs, Feedstuffs, Jul. 7, 2008, vol. 80, No. 27, pp. 12-13.
Barbosa, T.M., et al, "Screening for Bacillus Isolates in the Broiler Gastrointestinal Tract," Applied and Environmental Microbiology (2005), 72(2), 968-978.
Foster, J.W., et al., "Bacillus subtilis: An Avian Oral Pathogenicity and Toxicity Study in the Northern Bobwhite," Wildlife International Ltd., (1998) Easton, pp. 1-28, unpublished, Easton, Maryland, U.S.A.
Fritts, C.A., et al., "Bacillus subtilis C-3102 (Calsporin) Improves Live Performance and Microbiological Status of Broiler Chickens," J. Appl. Poult. Res., (2000) pp. 149-155, vol. 9, No. 2.
Ghosh, et al., "Bioaugmentation in the growth and water quality of livebearing ornamental fishes", Aquacult Int (2008) 16:pp. 393-403.
Guo, X., et al., "Screening of Bacillus Strains as Potential Probiotics and Subsequent Confirmation of the in vivo Effectiveness of Bacillus subtilis MA139 in Pigs," Antoine Van Leeuwenhoek, (Jul. 4, 2006) pp. 139-146, vol. 90, No. 2.

(Continued)

*Primary Examiner* — Janet Epps-Smith
(74) *Attorney, Agent, or Firm* — Adam L. Lunceford; Michelle L. Samonek

(57) ABSTRACT

The present invention relates to a method for enhancing the health of a human comprising administering to the human an effective amount of a composition comprising *Bacillus subtilis* QST713 or a mutant thereof.

15 Claims, 8 Drawing Sheets

(56) References Cited

OTHER PUBLICATIONS

Hinton, et al., "Comparison of in vitro inhibition of growth of salmonella typhimurium and *Escherichia coli* on chicken fee media by two sources of bacillus subtilis", [abstract] Poultry Science Meeting, 2006, 85 (Suppl. 1):192.

Hong, H.A., et al., "Bacillus subtilis Isolated from the Human Gastrointestinal Tract," Research in Microbiology, (2009) pp. 134-143, vol. 160.

Hong, H.A., et al., "The Use of Bacterial Spore Formers as Probiotics," FEMS Microbiology Reviews, (2005) pp. 813-835, vol. 29.

Jiraphocakul, S., et al., "Influence of a Dried Bacillus subtilis Culture and Antibiotics on Performance and Intestinal Microflora in Turkeys," Poult Sci., (Nov. 1990) pp. 1966-1973, vol. 69, No. 11.

Lund, B. et al., "Efficacy of GalliPro: A Microbial Feed Additive for Broilers," Proceedings of the 15th European Symposium on poultry nutrition, Balatonfüred, Hungary, Sep. 25-29, 2005.

Marrone, P.G., "Barriers to Adoption of Biological Control Agents and Biological Pesticides," CAB Reviews: Perspectives in Agriculture, Veterinary Science, Nutrition and Natural Resources Jul. 6, 2007, vol. 2. No. 51, p. 4, ISSN 1749-8848.

McLean, J., et al., "Benefits of Bacillus subtilis DSM 17299 (GalliPro) Supplementation in Chicken Diets," Proceedings of the 15th European Symposium on poultry nutrition, Balatonfüred, Hungary, Sep. 25-29, 2005.

Molnar, A.K., et al., "Influence of Bacillus subtilis on Broiler Performance," Proceedings of the 15th European Symposium on Poultry Nutrition, Balatonfüred, Hungary, Sep. 25-29, 2005.

Pan, Kangcheng, et al., "The Effects of Bacillus subtilis Additive on the Growth Performance, Carcass and Chicken Quality of the Broiler Chicken," (2005) pp. 11-14, vol. 20.

Setlow, et al., "Spores of Bacillus subtilis: Their Resistance to and Killing by Radiation, Heat and Chemicals," Journal of Applied Microbiology, vol. 101, Issue 3, pp. 514-525, Sep. 2006.

Shin, M.S., et al., "Isolation and Characterization of Bacteriocin-Producing Bacteria from the Gastrointestinal Tract of Broiler Chickens for Probiotic Use," Journal of Applied Microbiology (2008), 105, 2203-2212.

Wolfenden, R.E., et al., "Evaluation of a Screening and Selection Method for Bacillus Isolates for Use and Effective Direct-fed Microbials in Commercial Poultry," International Journal of Poultry Science (2010), 9(4), 317-323.

Yeow-Lim, et al., "Inhibition of Clostridium perfringens by a Novel Strain of Bacillus subtilis isolated from the Gastrointestinal Tracts of Healthy Chickens," Applied and Environmental Microbiology, Aug. 2005, pp. 4185-4190.

Zhou, Xiaohui, et al., "A Brief Analysis of Action Mechanism and Application Effect of Bacillus subtilis Formulation," Feed and Animal Husbandry, (2008) pp. 61-62, vol. 5.

European Search Report for EP Application No. 14163676.1 corresponding to PCT/US2009/057335, issued by the European Patent Office on Jun. 16, 2014.

Supplementary European Search Report for EP Application No. 09815204.4-2114 corresponding to PCT/US2009/057335, issued by the European Patent Office on Oct. 26, 2011.

International Search Report and Written Opinion of the International Searching Authority, International Patent Application No. PCT/US2009/057335, issued Jan. 12, 2010, 8 pages.

International Search Report and Written Opinion of the International Searching Authority, International Patent Application No. PCT/US2011/028755, issued Jul. 5, 2011, 12 pages.

* cited by examiner

METHOD FOR USING A *BACILLUS SUBTILIS* STRAIN FOR PROPHYLAXIS AND TREATMENT OF GASTRO-INTESTINAL CONDITIONS

CROSS-REFERENCE TO RELATED APPLICATIONS

This present application claims priority to U.S. Provisional Application No. 61/314,997, filed Mar. 17, 2010, in accordance with 35 U.S.C. Section 119(e). The foregoing application is hereby incorporated by reference in its entirety.

FIELD OF INVENTION

The present invention relates to the field of probiotics and their ability to improve human health, especially by preventing or treating gastro-intestinal disorders.

BACKGROUND OF INVENTION

The *Bacillus* genus comprises numerous endospore-forming bacteria that have myriad uses in the agricultural, animal nutrition and human health fields, among others. Several strain of *Bacillus* are currently marketed for use as probiotics to promote gut health. Although various commercial products contain strains of *Bacillus subtilis, Bacillus licheniformis*, and *Bacillus coagulans*, not all *Bacillus* strains are effective probiotics and must be evaluated on a case-by-case basis to determine safety and efficacy.

SUMMARY OF INVENTION

The present invention provides a strain of *Bacillus subtilis* which, when administered to a human, enhances the health of such human. Specifically, the present, invention relates to methods for enhancing the health of a human by administering to the human *Bacillus subtilis* QST713 or mutants thereof and/or metabolites of *Bacillus subtilis* QST713 or mutants thereof in an amount effective to treat or prevent gastrointestinal disorders. Such administration may reduce, alleviate or prevent symptoms of such disorders, such as diarrhea, abdominal cramping and inflammation of the gastrointestinal tract The compositions of the present invention may include *Bacillus subtilis* QST713 or mutants thereof and/or metabolites of *Bacillus subtilis* QST713 or mutants thereof In an amount effective to treat or prevent gastrointestinal disorders in combination with a earner, such as an enteric coating. Other compositions may include *Bacillus subtilis* QST713 or mutants thereof and/or metabolites of *Bacillus subtilis* QST713 or mutants thereof and (i) other probiotics, such as *Saccharomyces boulardii* (ii) a drug used to treat or prevent gastro-intestinal disorders, such as anti-inflammatory drugs or interferons, or (iii) food or a non-water beverage (such as milk or a beverage that is not composed of water only; such as lemonade, juice or tea) or baby formula.

In some embodiments, the compositions of the invention are administered in an amount effective to maintain health gut microflora. In others, they are administered in an amount effective to decrease the growth of pathogenic bacteria in the human or to modify the virulence factors of pathogenic bacteria such that virulence of the pathogen is attenuated.

Administration may be accomplished by eating or drinking the composition alone or in combination with food or drink or by swallowing a pill comprising the composition. In one embodiment, the drink is not water (and may be, for example, milk) or is not composed of water alone (and may be, for example, lemonade or juice or tea).

Administration of the compositions may occur for a relatively short period after a human suffers symptoms of a gastro-intestinal disorder in order to alleviate such symptoms. Administration, may also occur on a daily or other regular basis in order to prevent symptoms of a gastro-intestinal disorder from occurring or recurring.

BRIEF DESCRIPTION OF THE DRAWINGS

Figure 1:
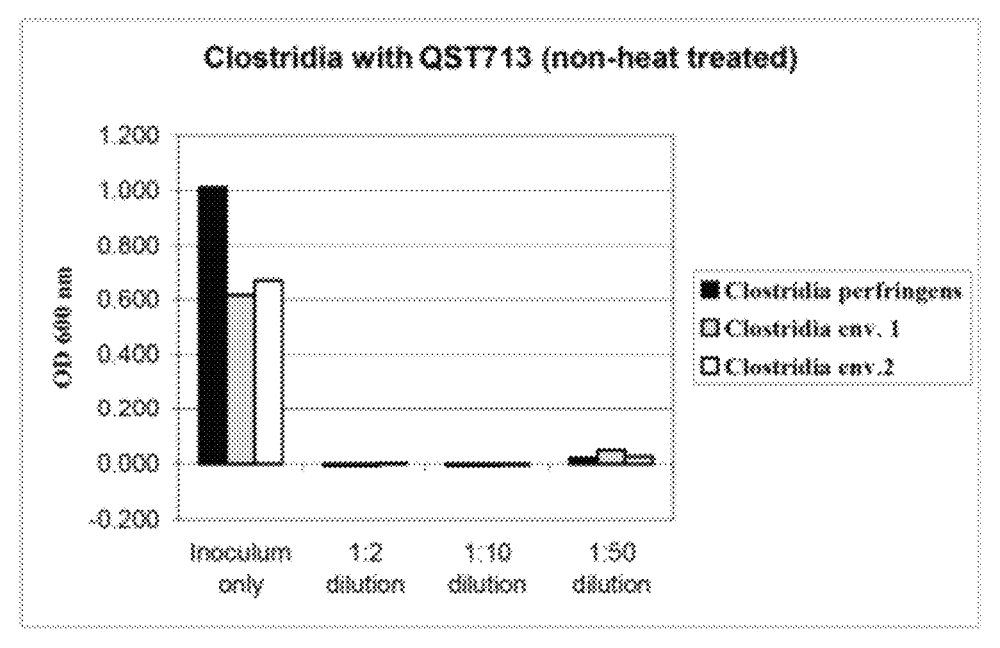

FIG. 1 shows results of a test of a cell-free preparation of *Bacillus subtilis* QST713 for efficacy against various isolates of *Clostridia*.

Figure 2:
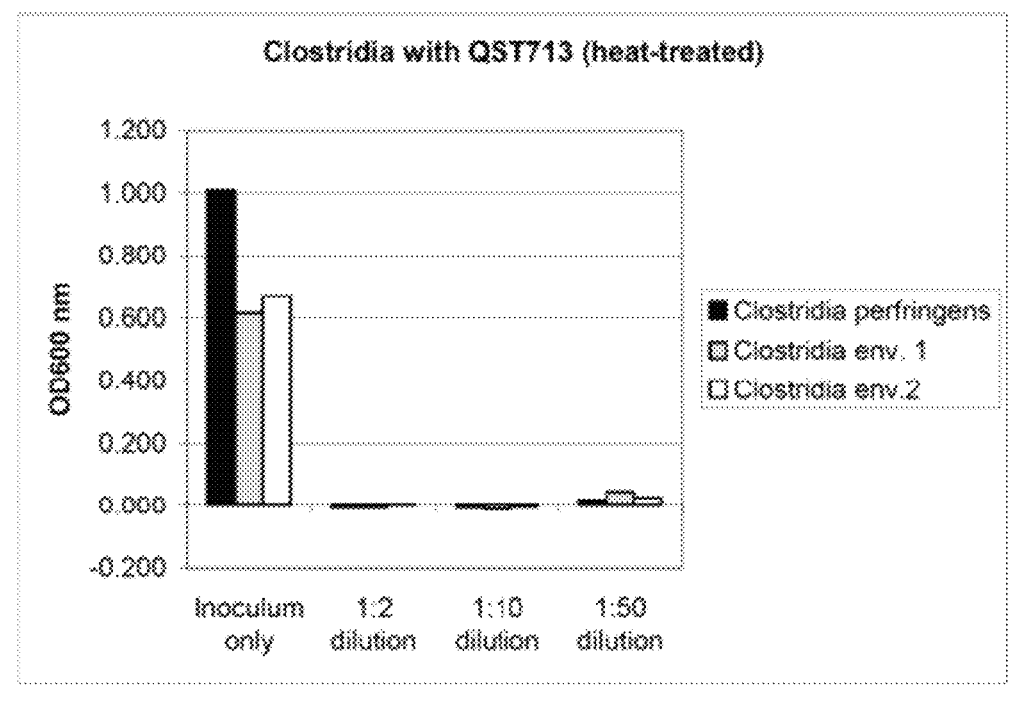

FIG. 2 represents results of a test of a heat-treated cell-free preparation of *Bacillus subtilis* QST713 for efficacy against various isolates of Clostridia.

DETAILED DESCRIPTION OF INVENTION

Figure 3:
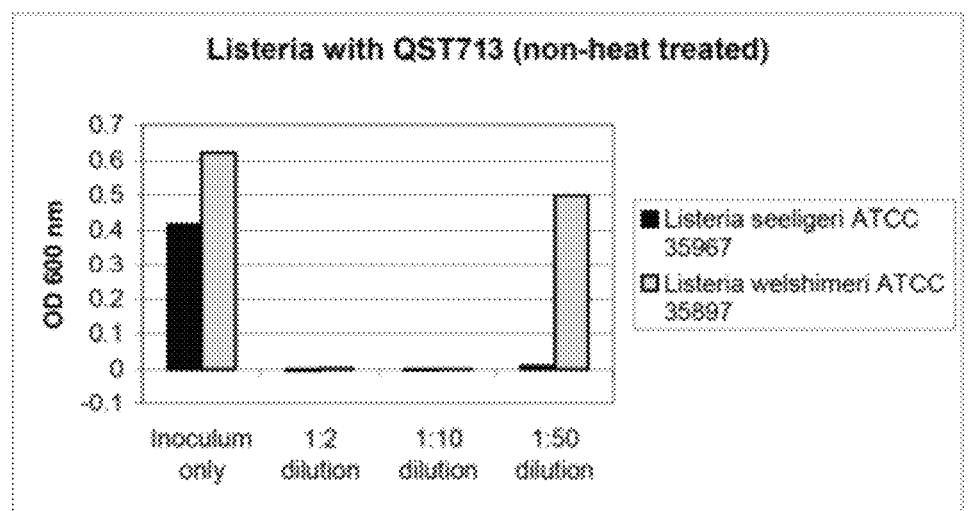
FIG. 3 shows results of a test of a cell-free preparation of *Bacillus subtilis* QST713 for efficacy against various isolates of *Listeria*.
Figure 4:
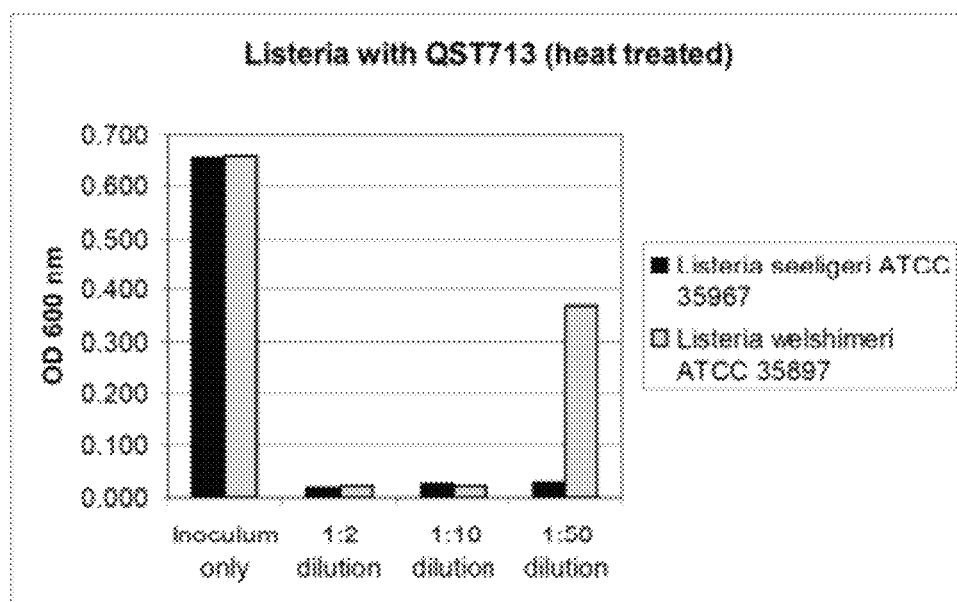
FIG. 4 represents results of a test of a heat-treated cell-free preparation of *Bacillus subtilis* QST713 for efficacy against various isolates of *Listeria*.
Figure 5:
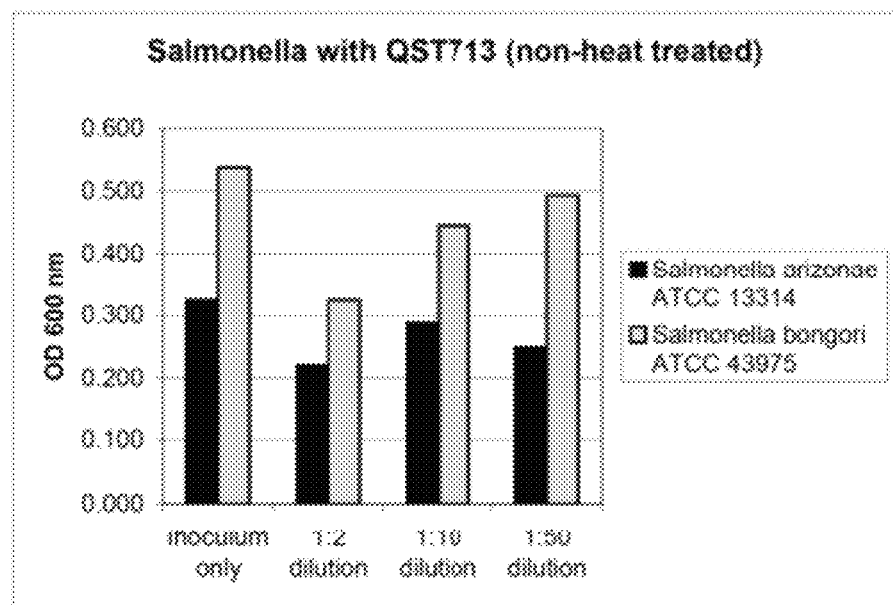
FIG. 5 shows results of a test of a cell-free preparation of *Bacillus subtilis* QST713 for efficacy against various isolates of *Salmonella*.
Figure 6:
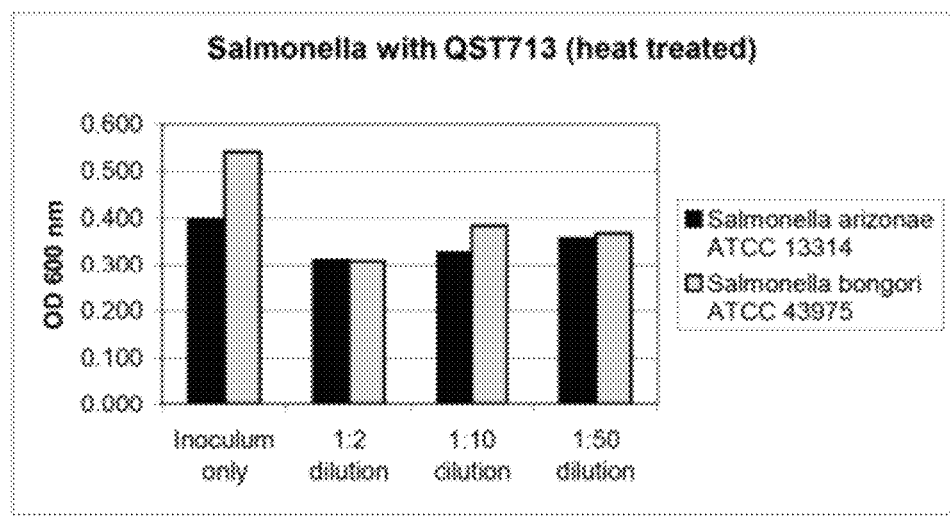
FIG. 6 represents results of a test of a heat-treated cell-free preparation of *Bacillus subtilis* QST713 for efficacy against various isolates of *Salmonella*.

The present invention relates to a novel use of *Bacillus subtilis* strain QST713 and/or its metabolites that are effective to enhance human health as a probiotic. Probiotics are used in human health applications in order to maintain healthy gut microflora, including a reduction in detrimental bacteria such as *Clostridia dificile*, and to alleviate the symptoms of gastrointestinal disorders.

The present invention encompasses a (therapeutic or non-therapeutic) method for enhancing human health by administering to a patient a composition comprising (i) *Bacillus subtilis* QST713, (ii) mutants of *Bacillus subtilis* QST713, (iii) cell-free preparations of (i) or (ii), or (iv) metabolites of (i) or (ii).

*Bacillus subtilis* QST713, its mutants, its supernatants, and its metabolites, and methods for their use to control plant pathogens and insects are fully-described in U.S. Pat. Nos. 6,060,051, 6103,228, 6,291,426, 6,417,163, and 6,638, 910. In these patents, the strain is referred to as AQ713. *Bacillus subtilis* QST713 has been deposited with the NRRL on May 7, 1997 under the provisions of the Budapest Treaty on the International Recognition of the Deposit of Microorganisms for the Purpose of Patent Procedure under Accession Number B21661. Any references in this specification to QST713 refer to *Bacillus subtilis* QST713.

The *Bacillus subtilis* QST713 strain has certain properties, which, surprisingly, have been found to make the strain well-suited for enhancing human health. Spores of QST713 are viable at low pHs and cells of QST713 grow (given conducive nutrient conditions) at pHs as low as 4.5. QST713 also has the ability to aggregate, or swarm, as shown in Example 2, thereby outcompeting and reducing pathogenic bacteria. Without wishing to be limited by any particular theory, it is thought that *Bacillus subtilis* QST713 enhances human health by a multifaceted mode of action, including (i) producing antibacterial metabolites, (ii) competing with pathogens by using more nutrients and/or attachment spaces than the pathogens, thereby preventing effective establishment of pathogenic bacteria in the gut, (iii) immunomodulation, and/or (iv) modification of virulence factors of bacterial pathogens in such a manner that virulence of the pathogens is attenuated.

In one aspect of the invention, compositions administered to humans comprise mutants of *Bacillus subtilis* QST713 having all the identifying characteristics of QST713. Such mutants may have DNA sequence identity to QST713 of at least about 90%, at least about 91%, at least about 92%, at least about 93%, at least about 94%, at least about 95%, at least about 96%, at least about 97%, at least about 98%, or at least about 99%. In some embodiments, mutants are spontaneous mutants. The teen spontaneous mutant refers to mutants that arise from QST713 without the intentional use of mutagens. Such spontaneous mutants may be obtained by classical methods, such as growing the *Bacillus subtilis* strain in the presence of a certain antibiotic to which the parent, is susceptible and testing any resistant mutants for improved biological activity or, in this application, improved ability to enhance human health including by reducing the symptoms of gastrointestinal disorders. Other methods for identifying spontaneous mutants will be known to those of ordinary skill in the art.

All references in this application to *Bacillus subtilis* QST713 or its mutants refer to bacteria that have been isolated from nature and are grown by humans, for example, in the laboratory or under industrial conditions.

*Bacillus subtilis* QST713 cells may be present in the compositions of the present invention as spores (which are dormant), as vegetative cells (which are growing), as transition state ceils (which are transitioning from growth phase to sporulation phase) or as a combination of all of these types of cells. In some embodiments, the composition comprises mainly spores. In other embodiments, the composition comprises spores and metabolites produced by the cells during fermentation before they sporulate, as described below.

Metabolites of QST713 or its mutants include lipopeptides, such as iturins, surfactins, plipastatins, and agrastatins and other compounds with antibacterial properties. Lipopeptide metabolites of QST713 are described in detail in U.S. Pat. Nos. 6,291,426 and 6,638,910.

Compositions of the present invention can be obtained by culturing *Bacillus subtilis* QST713 or its mutants according to methods well known in the art, including by using the media and other methods described in U.S. Pat. No. 6,060,051. Conventional large-scale microbial culture processes include submerged fermentation, solid state fermentation, or liquid surface culture. Towards the end of fermentation, as nutrients are depleted, *Bacillus subtilis* QST713 cells begin the transition from growth phase to sporulation phase, such that the final product of fermentation is largely spores, metabolites and residual fermentation medium. Sporulation is part of the natural life cycle of this *Bacillus subtilis* and is generally initiated by the cell in response to nutrient limitation. Fermentation is configured to obtain high levels of colony forming units of *Bacillus subtilis* QST713 and to promote sporulation. The bacterial cells, spores and metabolites in culture media resulting from fermentation may be used directly or concentrated by conventional industrial methods, such as centrifugation, tangential-flow filtration, depth filtration, and evaporation. In some embodiments, the concentrated fermentation broth is washed, for example via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation. The resulting dry products may be further processed, such as by milling or granulation, to achieve a specific particle size or physical format. Carriers, described below, may also be added post-drying.

Cell-tree preparations of fermentation broth of QST713 can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its administration to humans. Concentration methods and drying techniques described above for fermentation broth are also applicable to cell-free preparations.

Metabolites of QST713 can be obtained according to the methods set forth in U.S. Pat. No. 6,060,051. The term "metabolites" as used herein may refer to semi-pure and pure or essentially pure metabolites, or to metabolites that have not been separated from *Bacillus subtilis* QST713. The lipopeptides and other bacteriacidal metabolites of QST713 are between 600 kilodaltons and 100 daltons. Therefore, in some embodiments, after a cell-tree preparation is made by centrifugation of fermentation broth of QST713, the metabolites may be purified, by size exclusion filtration that groups metabolites into different fractions based on molecular weight cut-off, such as molecular weight of less than 600 kDa, less than 500 kDa, less than 400 kDa and so on. Concentration methods and drying techniques described above for formulation of fermentation broth are also applicable to metabolites.

Compositions of the present invention may include carriers, which are inert formulation ingredients added to compositions comprising cells, cell-free preparations or metabolites to improve recovery, efficacy, or physical properties and/or to aid in packaging and administration. Such carriers may be added individually or in combination. In some embodiments, the carriers are added after concentrating fermentation broth and during and/or after drying. Conventional solid carriers are silicone, starch, talc, calcium phosphate, calcium sulfate, magnesium stearate, stearic acid, methyl cellulose, alginates, dextrans, acacia gum and other conventional carriers well known to those of ordinary skill in this art. Other formulation ingredients such as diluents, binders, lubricants, colors and flavoring agents may also be used.

In one embodiment, compositions of the present invention may be in the form of solid preparations, such as capsules, tablets, powders, granules and wafers, or liquid preparations, such as suspensions. Compositions of the present invention may also be incorporated into food or drink, including a medical food prescribed by a physician for a patient's particular nutritional needs, baby formula, health foods, and dietary supplements. Alternatively, compositions may be prepared in a powdered, granular or liquid form for mixture with food or drink, such as water or non-water beverages (i.e., beverages that are not produced with water or do not consist of water alone), immediately before consumption.

In embodiments in which the composition comprises metabolites of QST713 or its mutants or vegetative cells of QST713 or is mutants, or cell-free preparations of QST713 or its mutants, it may be formulated with an enteric coating which remains intact in the stomach but dissolves and releases metabolites, such as bacteriocins and/or lipopeptides, and/or vegetative cells, once it reaches the small intestine or the large intestine.

In embodiments in which the compositions are formulated separately from food or drink; the concentration on a weight by weight basis (w/w) of (i) Bacillus subtilis QST713 or its mutants, (ii) cell-free preparations of QST713 or its mutants, (iii) metabolites of QST713 or its mutants or (iv) combinations of cells and metabolites in the formulated composition may be about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17% about 18%, about 19%, about 20% about 25%, about 30%, about, 35%, about 40%, about 45%, about 50%, about 55%, about 60%, about 65%, about 70%, about 75%, about 80%, about 85%, about 90%, or about 95%. In some embodiments, for example., where the concentrated formulation broth has been washed and dried without heat, such as via freeze drying, the concentration of Bacillus subtilis QST713 or its mutants in the final composition may be from about 90% to about 100%.

The compositions of the present invention may be administered/fed to humans to improve gut health or the general overall, physical condition of such human. The compositions can be administered both for therapeutic and non-therapeutic applications. An effective amount of a composition is an amount effective to enhance the health of a human in comparison to a human that has not been administered the composition but otherwise has been administered the same diet as has the human receiving the compositions of the present, invention and has the same disorder or symptoms or is at the same risk for the disorder as the human administered the composition. Alternatively, an effective amount is the amount needed to prevent recurrence or to reduce symptoms of gastrointestinal disorders.

In one embodiment, the composition is used to enhance the health of a human suffering from oral risk for a gastro-intestinal disorder by reducing the symptoms of such disorder or reducing the rate of occurrence or recurrence of such disorder. Gastro-intestinal disorders include acute diarrhea, such as traveler's diarrhea or gastroenteritis caused by food poisoning or flu, inflammatory bowel disease, irritable bowel disorder, antibiotic-associated diarrhea, and Clostridium dificile associated diarrhea. The primary forms of irritable bowel disease are Crohn's disease and ulcerative colitis. Symptoms of such gastrointestinal disorders are well known and include diarrhea, abdominal pain, weight loss, inflammation of the gastrointestinal tract and vomiting.

Thus, in line with the above, embodiments of the present application are directed to non-therapeutic methods such as restoring normal weight gain, maintaining healthy gut microflora, reducing diarrhea, and decreasing inflammation of the gastro-intestinal tract by administering/feeding to the human a composition comprising Bacillus subtilis QST713, a mutant of Bacillus subtilis QST713, a cell-free preparation derived from Bacillus subtilis QST713 or its mutant, or metabolites of QST713 or its mutants.

Maintenance of gut microflora refers to decreasing (by killing or inhibiting the growth of) harmful, disease-causing microorganisms of public health concern and/or increasing or maintaining healthy levels of beneficial bacteria, such as Lactobacilli and Bifidobacteria, as compared to a human to which the methods of this invention have not been applied. Without wishing to be bound, by any particular theory, it is thought that increases to beneficial bacteria may be caused by stimulating growth of such bacteria or simply by selectively decreasing pathogenic bacteria, thereby giving the beneficial bacteria more space to grow and to attach to the gut wall and/or more efficient access to nutrients and growth factors. In addition, or alternatively, beneficial bacteria may modify the virulence factors of pathogenic bacteria, thus decreasing the virulence of the pathogenic bacteria. Harmful, disease-causing bacteria that may be decreased by the methods of this invention include Clostridia spp. (such as perfringens and dificile), Listeria spp. (such as moncytogenes, seeligeri and welshimeri), Salmonella spp. (such as enterica, arizonae, typhirium, enteritidis and bonglori), E. coli, Enterococus spp. (such as faecalis and faecium), Campylobacter, Aeromonas spp., Staphylococcus aureus, Shigella dysenteria and Vibrio spp. In some embodiments, harmful, disease-causing microorganisms may be reduced by about 0.5 log, about 1 log, about 2 log, about 3 log, about 4 log, or about 5 log.

The methods of the present invention may also be used to restore normal intestinal balance after administration of therapeutic amounts of antibiotics by inhibiting growth of pathogenic bacteria and/or increasing or maintaining growth of beneficial bacteria. The term "therapeutic amount" refers to an amount sufficient to ameliorate or reverse a disease state in a human.

In another aspect, compositions of the present invention comprising Bacillus subtilis QST713, its mutants, cell-free preparations of QST713 and its mutants and metabolites of QST713 and its mutants may further include or be administered with other probiotics, such as other bacterial spore formers, or with prebiotics. Examples of probiotics are provided in Hong, H. A., et al., "The use of bacterial spore formers as probiotics" FEMS Microbiology Reviews 29 (2005) 813-835. Prebiotics are compounds that stimulate the growth and/or activity of Bacillus subtilis QST713 or its mutants in the gut, such as oligosaccharides, including inulin, fructooligosaccharides. galactooligosaccharides and soybean oligosaccharides, and free nucleotides.

In another aspect, the compositions of the present invention may include or be administered with (either at the same time or at different times) anti-diarrheal agents, anti-gas agents, dietary fibers, antibiotics, such as methotrexate, anti-inflammatory drugs, amino acids, electrolytes, vitamins and minerals.

In embodiments in which the compositions comprise QST713 or its mutants, the bacteria should be administered in an amount that is effective to enhance human health. In embodiments in which the compositions are being administered to treat or prevent gastrointestinal disorders, they should be administered to a patient, suffering from such disorder or at risk for such disorder at a dose of from about $1 \times 1^3$ CFU Bacillus subtilis per kilogram body weight to about $1 \times 10^{15}$ Bacillus subtilis per kilogram body weight, in another embodiment from about $1 \times 10^4$ CFU Bacillus subtilis per kilogram to about $1 \times 10^{11}$ Bacillus subtilis per kilogram should be administered. In yet another from about $1 \times 10^5$ CFU Bacillus subtilis per kilogram to about $1 \times 10^{10}$ Bacillus subtilis per kilogram should be administered. In yet another from about $1 \times 10^6$ if CFU Bacillus subtilis per kilogram to about $1\times10^9$ Bacillus subtilis per kilogram should be administered. In some embodiments the dose is about $1\times10^3$ CFU Bacillus subtilis per kilogram body weight, about $1\times10^4$ or about $1\times10^5$ or about $1\times10^6$ or about $1\times10^7$ or about $1\times10^8$ or about $1\times10^9$ or about $1\times10^{10}$ or about $1\times10^{11}$ or about $1\times10^{12}$ CFU Bacillus subtilis per kilogram. The compositions are typically administered orally and daily at the above doses for several days. The compositions may be administered on a longer term basis after symptoms are initially alleviated at a lower dose than was used, initially. For preventative purposes, the compositions may be administered on a daily or other regular basis.

The compositions of the present invention can also be administered orally as a pharmaceutical in combination with a pharmaceutically acceptable carrier. Optimal dosage levels can easily be determined by those skilled in the art, by evaluating, among other things, the composition's ability to (i) inhibit or reduce pathogenic bacteria in the gut at various doses, (ii) increase or maintain levels of beneficial bacteria and/or (ii) enhance human health at various doses.

The following examples are given for purely illustrative and non-limiting purposes of the present invention.

EXAMPLES

Example 1

In vitro Studies of Efficacy of QST713 Cell-Free Preparations against Pathogens

Cell-free preparations of QST713 were tested for antimicrobial activity against Clostridia (Clostridia perfringens ATCC13124 and two environmental isolates of Clostridia perfringens); Listeria (Listeria moncytogenes ATCC 19116 and 19111, Listeria seeligeri ATCC 35968 and Listeria welshimeri ATCC 35897); Salmonella (Salmonella enterica ATCC 10398, Salmonella arizonae ATCC 13314 and Salmonella bongori ATCC 43975); and E. coli, using Kirby-Bauer and minimal inhibitory concentration (MIC) techniques.

Cell-free preparations were prepared by growing QST713 in media corresponding to media in which the target pathogen was grown, as shown in Table 1, below, centrifuging the culture for 15 minutes at 3000 rpm at 23 C and filtering it through a 0.45 μm Nalgene filter unit. To test for heat stability, a portion of the cell-free preparation was heated to 50° C. for one hour before each of the Kirby-Bauer and MIC tests.

TABLE 2

| Genus | Species/ATCC | Growth Media | Conditions for Growth |
|---|---|---|---|
| Clostridia | Perfringens ATCC 13124 | Reinforced Clostridial Medium (Oxoid Cat. No. CM0149). | Overnight growth in the AnaeroPak jar as above with 1 sachet of MGC Anaero-Indicator (Remel Cat. No. 68-3001) |
| Clostridia | Perfringens environmental isolate | Same as above | Same as above |
| Clostridia | Perfringens environmental isolate | Same as above | Same as above |
| Listeria | monocytogenes ATCC 19116 | Brain heart infusion broth | Overnight at 37° C. |

TABLE 2-continued

| Genus | Species/ATCC | Growth Media | Conditions for Growth |
|---|---|---|---|
| Listeria | monocytogenes ATCC 19111 | Same as above | Same as above |
| Listeria | seeligeri ATCC 35968 | Same as above | Same as above |
| Listeria | welshimeri ATCC 35897 | Same as above | Same as above |
| Salmonella | enterica ATCC 10398 | Trypticase Soy Broth | Same as above |
| Salmonella | arizonae ATCC 13314 | Same as above | Same as above |
| Salmonella | bongori ATCC 43975 | Same as above | Same as above |

In the Kirby-Bauer experiments, 2 mm sterile filter paper disks were immersed in QST713 supernatant and air-dried under sterile conditions. These disks were then placed on lawns of the target pathogen, incubated overnight and zones of inhibition measured. Zones of inhibition were observed for the Clostridia and Listeria targets.

In the MIC technique, wells of microliter plates were inoculated with 75 ul of each target pathogen, diluted to $1\times10^5$. The above-described cell-free preparation was added to each well at final dilutions of 1:2, 1:10 and 1:50. Plates were incubated overnight at 37° C. and OD600 and read with a Wallach microtitre reader. The cell-free preparation (both heat-treated and non-heat treated) was significantly effective against the Clostridia and Listeria targets and inhibited growth of Salmonella and E. coli, although no zones of inhibition were observed for these last two pathogens on Kirby-Bauer plates. Data for Clostridia, Listeria and Salmonella are shown in FIGS. 1-6.

Example 2

In vitro Studies of Efficacy of QST713 Against Various Bacteria

A powder formulation of Bacillus subtilis QST713 was tested for efficacy against various environmental isolates of the following bacteria: Clostridium perfringens, Escherichia coli, Salmonella enteritidis, Campylobacter jejuni, and Listeria monocytogenes. This powder formulation was prepared by fermenting Bacillus subtilis QST713 (such that towards the end of fermentation, as nutrients are depleted, Bacillus subtilis QST713 cells begin the transition from growth phase to sporulation phase, such that the final product of fermentation is largely spores, metabolites and residual fermentation medium), concentrating the fermentation broth, and drying, as described above in the Detailed Description of invention. It had 14.6% concentrated, dried broth and 85.4% formulation inerts (chosen from the possibilities described above) and contained at a minimum approximately $7.3\times10^9$ CFU Bacillus subtilis /gram and at a maximum approximately $1\times10^{10}$ CFU Bacillus subtilis /gram. This formulation shall be referred to herein as Composition 1. Stock solutions of Composition 1 were prepared by adding 0.2 gram of the formulated powder to 1.8 ml of sterile distilled water, such that the solution contained roughly $1\times10^9$ CFU Bacillus subtilis per ml. Test organisms were streaked to trypticase soy agar with 5% sheep blood with up to four organisms streaked to a single agar plate each in a single line that bisects the agar plate. The organisms were allowed to dry overnight. Then, the inoculated plates were streaked with the suspension of formulated QST713 described above, which was swabbed perpendicular to the test organisms. The

Figure 7:
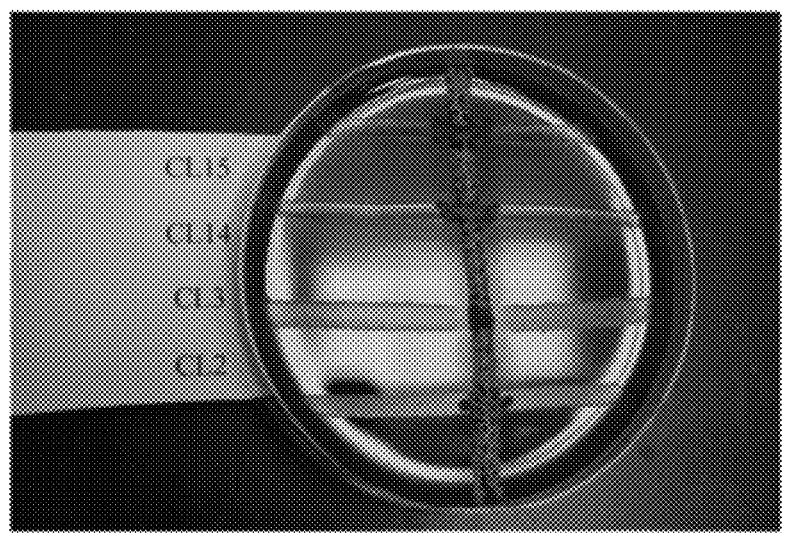
FIG. 7 shows agar plates on which *Bacillus subtilis* QST713 (vertical) and various isolates of *Clostridium perfringens* (horizontal) were cross streaked in order to test efficacy of QST713 against the pathogens.
Figure 8:
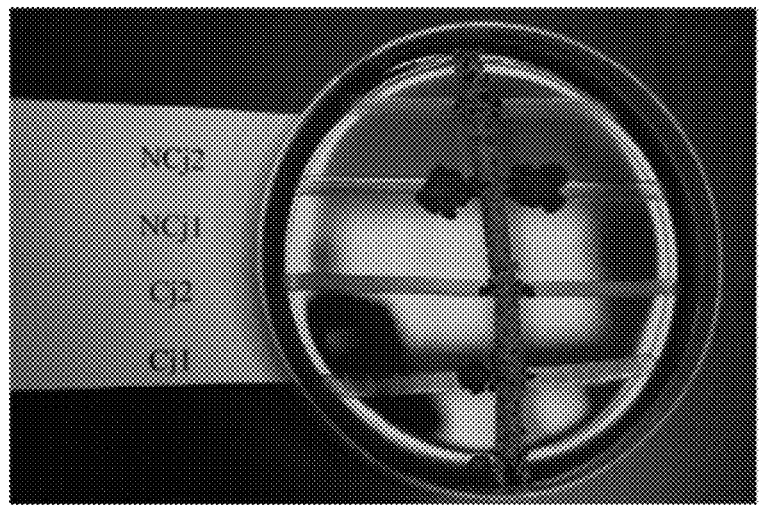
FIG. 8 shows agar plates on which *Bacillus subtilis* QST713 (vertical) and various isolates of *Campylobacter jejuni* (horizontal) were cross streaked in order to test, efficacy of QST713 against the pathogens.

*Clostridium perfringens* and *Campylobacter jejuni* isolates were incubated in a Campy gas atmosphere (10% CO2, 5% O2, 8% N2) at 41±2 C overnight. The other isolates, which are aerobic, were incubated in 36±2 overnight without Campy gas. QST713 caused inhibition of several of the isolates of *Clostridium perfringens, Salmonella enteritidis, Campylobacter jejuni* and *Listeria monocytogenes*, although no inhibition of *E. coli*. In addition, in some cases *Bacillus subtilis* QST713 showed aggressive competitive overgrowth of the pathogenic bacteria. Results are summarized in the table below. The zones of inhibition reported in the table were measured from the edge of the *Bacillus* growth to the beginning of growth of the test organism. In addition, photographs of the *Clostridium perfringens* and *Campylobacter jejuni* plates are shown in FIGS. 7 and 8, respectively.

TABLE 3

| Culture Name | Isolate ID | Atmosphere and Temperature | Zone of inhibition (mm) | Comments |
|---|---|---|---|---|
| *Clostridium perfringens* | CL-2 | Campy gas, 41° C. | 0 | Slight inhibition of growth although no zone, *Bacillus* swarming |
|  | CL-3 |  | 3 |  |
|  | CL-14 |  | 0 | *Bacillus* swarming |
|  | CL-15 |  | 0 | *Bacillus* swarming |
| *Escherichia coli* O157 | EC-80 | Aerobic, 36° C. | 0 |  |
|  | EC-81 |  | 0 |  |
|  | EC-82 |  | 0 |  |
| *Salmonella enteritidis* | SE 27 | Aerobic, 36° C. | 0 |  |
|  | SE 28 |  | 2 |  |
|  | SE 29 |  | 1 |  |
|  | SE 03 |  | 1 |  |
|  | SE 09 |  | 1 |  |
|  | SE 22 |  | 0 |  |
| *Campylobacter jejuni* | Cj-1 | Campy gas, 41° C. | 1 | *Bacillus* swarming |
|  | Cj-2 |  | 0 | Slight inhibition of growth although no zone, *Bacillus* swarming |
|  | NCj1 |  | 0 | *Bacillus* swarming |
|  | NCj2 |  | 1 |  |
| *Listeria monocytogenes* | LM 1 | Aerobic, 36° C. | 2 |  |

Example 3

Determination of the Efficacy of Orally Administered *Bacillus* QST713 in the Treatment of Induced Colitis in Rats (a Model for Colitis in Humans)

Prophetic Example

In this experiment, the efficacy of QST713 will be studied against colitis in rats induced by the rectal administration of 2,4,5-trinitrobenzene sulfonic acid (TNBS).

Study Design:

Male Wistar white rats are used throughout this study. At the beginning of the treatment period, the animals are 10 to 12 weeks old. Upon their arrival at the test facility, the animals are given a complete clinical examination under the supervision of a veterinarian to ensure that they are in good condition. The animals are acclimatized to the study conditions for a period of at least 7 days. Animals are randomized and allocated to polycarbonate cages (Length 42.1×Width 290×Height 190 mm). The animal room and test room conditions are set as follows: temperature: 22±3 degrees C., relative humidity: 50±20%, light/dark cycle: 12 hr/12 hr (light 07.00 AM-19.00 PM) and ventilation: approximately 7 cycles/hour of filtered, non-recycled air. All animals have free access (except for the overnight fasting prior to TNBS administration) to rat pellet feed and purified water ad libitum.

In replicated trials the day of induction of colitis is set as day 1. Colitis is induced, after an overnight fast, using a single intrarectal administration of TNBS at 100 mg/Kg body weight, 8 cm proximal to the anus. The colitis-negative control groups are given saline intrarectally (0.5 ml per animal once) on day 1. Colitis-negative and colitis-positive control groups are given distilled water orally at 10 ml/kg, 3 times daily with 4 h inter dosing, starting on day 1 and up to and including day 7.

In the replicated trials, groups with TNBS-induced colitis are treated with QST713 (1.5×10 E8 CFU/Kg or 1.5×10 E9 CFU/Kg respectively), 3 times daily with 4-h interdosing, starting on day 1 and up to and including day 7; with mesalazine (250 mg/Kg/day), starting on day 1 and up to and including day 7; with infliximab (3 mg/Kg) as a single dose on day 1 or with *S. boulardii* (1.5×10 E8 CFU/Kg), 3 times daily with 4 h inter dosing, starting on day 1 and up to and including day 7.

The first or only (in case of infliximab) dose of treatment is given within 2 hours (distilled water, QST713, *S. boulardii* and mesalazine) or 3 hours (infliximab) after administration of TNBS. Except for infliximab, which was injected intravenously, all treatments are administered by gavage. Twice daily observations are made for clinical signs and mortality. Body weights of animals are recorded on days 1, 4 and 7. On day 8 animals are sacrificed and a 5 cm long segment of the colon (from 10 to 5 cm proximal to the anus) is excised. These segments were opened longitudinally. Contents are removed by washing with saline and gross morphology is scored using the following scale: 0=no ulcers or inflammation, 1=no ulcers only local hyperaemia, 2=ulceration without hyperaemia, 3=ulceration and inflammation at one site only, 4=two or more sites of ulceration and inflammation, and 5=ulceration extending more than 2 cm. The weight of each 5 cm colonic segment is also recorded to assess Inflammatory induced edema.

Test Preparations

TNBS 5% (w/v) in water (Sigma-aldrich, St Louis, USA) is diluted to a 2.5% solution with ethanol 50%. Dose volume is 4 ml/Kg body weight. QST713 (AgraQuest Inc. Davis, Calif. USA) fermentation broth dried on a malto- and cyclodextrin carrier, is suspended in distilled water to concentrations of 1.5×10 E7 and 1.5×10 E8 CFU/ml. Dose volume is 10 ml/Kg body weight, *Saccharomyces boulardii* (Enterol™, Biodiphar, Brussel, Belgium) is suspended in distilled water to a concentration of 1.5×10 E7 CFU/ml. Dose volume is 10 ml/Kg body weight. Mesalazine (Mesacol™, Sun Pharmaceutical Ind. Ltd, Mumbai, India) tablets are powdered using pestle and mortar and a solution in distilled water is prepared containing 25 mg 5-aminosalicylic acid per ml. Dose volume is 10 ml/Kg body weight. Remicade RTM (infliximab) (Centocor B. V., Leiden, The Netherlands) is first reconstituted with 10 ml water for injection and is further diluted to 2 mg/ml concentration using saline. Dose volume employed is 1.5 ml/Kg body weight. All body weight dependant doses are administered on the basis of the last individual body weight taken. Fresh preparations are made prior to each administration. The preparations are stirred vigorously before each dosing.

Expected Results and Discussion:

Some animals show mild signs of diarrhea after induction of colitis with TNBS. The number of observations of diarrhea recorded (and the number of animals affected) in the different treatment groups from day 1 up to and including day 7 are recorded. The colitis-positive control groups show substantial body weight loss accompanying the colitis. While treatments all significantly suppress the negative effect of colitis on body weight gain, it is expected that the QST713 treatment will show statistically significant reductions in diarrhea and improved weight gain. It is expected that QST713 and mesalazine always result in a colon segment weight and a gross morphology score for the colon wall that could be clearly distinguished from those of the colitis-positive control group.

It is expected that the health status of the colon wall in rats with TNBS induced colitis treated with QST713 and Mesacol is macroscopically the same as that in colitis-free rats. Visual examinations of the longitudinally opened colon segments are expected to show the ulcerations and areas of necrotic tissue present in the positive control, the *S. boulardii*, and the infliximab treatment groups and the absence thereof in the QST713 groups and the mesalazine group. At the end of the treatment period the average body weight gain and colon segment weight data of rats treated with infliximab are intermediary to those of the colitis-negative and the colitis-positive control groups in both trials. In the colon segments of rats treated with QST713 it is expected that there are no ulcerations, and only hyperaemia is observed in the majority of these segments. QST713 is expected to clearly attenuate inflammation in the rat colon wall as induced by intrarectal administration of TNBS and, at least as to the higher dosage rate, to an extent that the data from this treatment cannot be statistically discerned from those of the colitis-negative control group.

CONCLUSION

This study will be designed and conducted to confirm and document the efficacy of *Bacillus* 'QST713' against 2,4,6-trinitrobenzenesulfonic acid (TNBS)-induced colitis in rats as well as to compare its efficacy with that of *S. boulardii* (probiotic), mesalazine and infliximab (standard drugs). This rat model is well established, reliable and widely used to examine the efficiency of drugs aimed at treating IBD. Without any treatment after induction of colitis several rats will likely show mild signs of diarrhea and on average keep losing weight throughout the remaining trial period. The gross morphology of the intestinal wall of their colon will likely be characterized by inflammation, ulceration and even necrosis. It is expected that sequential treatment with, three doses of QST713 at 1.5×1.0 E8 CFU/Kg/day or 3 times 1.5×10 E9 CFU/Kg/day will result in a colon wall health status that is statistically identical to that of the negative control group and that of the group treated with the standard drug mesalazine, an anti-inflammatory.

We claim:

1. A method for enhancing the health of a human suffering from a gastrointestinal disorder associated with a *Campylobacter jejuni* infection comprising:
    administering to the human an effective amount of a composition comprising *Bacillus subtilis* QST713 (NRRL Accession Number B21661) or a mutant of *Bacillus subtilis* QST713
    wherein
    the mutant has DNA sequence identity to *Bacillus subtilis* QST713 of at least about 98%;
    the effective amount is at least $1.5 \times 10^8$ colony forming units (CFU) per kg; and
    administering the composition reduces or alleviates at least one symptom of the gastro-intestinal disorder associated with the *Campylobacter jejuni* infection.

2. The method of claim 1 wherein the composition comprises the *Bacillus subtilis* QST713.

3. The method of claim 2 wherein the composition further comprises metabolites produced by the *Bacillus subtilis* QST713.

4. The method of claim 1 wherein the symptom is diarrhea.

5. The method of claim 1 wherein the symptom is abdominal cramping.

6. The method of claim 1 wherein the symptom is inflammation of the gastrointestinal tract.

7. The method of claim 1 wherein the gastro-intestinal disorder is selected from the group consisting of acute diarrhea, inflammatory bowel disease, irritable bowel disorder, and antibiotic-associated diarrhea.

8. The method of claim 1 wherein the composition is administered in an amount effective to maintain healthy gut microflora.

9. The method of claim 1 wherein the composition further comprises a carrier.

10. The method of claim 1 wherein the composition is administered with other probiotics.

11. The method of claim 10 wherein the other probiotic is *Saccharomyces boulardii*.

12. The method of claim 1 wherein the composition is administered with a drug used to prevent or treat gastro-intestinal disorders.

13. The method of claim 12 wherein the drug is an antibiotic or an anti-inflammatory.

14. The method of claim 13 wherein the composition is administered after completion of administration of the antibiotic.

15. The method of claim 1 wherein the effective amount is at least $1.5 \times 10^9$ CFU per kg.

* * * * *